United States Patent
Nakai et al.

(10) Patent No.: US 11,660,002 B2
(45) Date of Patent: May 30, 2023

(54) COMPOSITION FOR ACOUSTIC WAVE PROBE, SILICONE RESIN FOR ACOUSTIC WAVE PROBE FORMED OF THE SAME, ACOUSTIC WAVE PROBE, ULTRASOUND PROBE, ACOUSTIC WAVE MEASUREMENT APPARATUS, ULTRASOUND DIAGNOSTIC APPARATUS, PHOTOACOUSTIC WAVE MEASUREMENT APPARATUS, AND ULTRASOUND ENDOSCOPE

(71) Applicant: FUJIFILM Corporation, Tokyo (JP)

(72) Inventors: Yoshihiro Nakai, Kanagawa (JP); Atsushi Hashimoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1108 days.

(21) Appl. No.: 16/353,204

(22) Filed: Mar. 14, 2019

(65) Prior Publication Data

US 2019/0200876 A1 Jul. 4, 2019

Related U.S. Application Data

(63) Continuation of application No. PCT/JP2017/033325, filed on Sep. 14, 2017.

(30) Foreign Application Priority Data

Sep. 20, 2016 (JP) ............................. JP2016-183062

(51) Int. Cl.
| | |
|---|---|
| *A61B 5/00* | (2006.01) |
| *C08L 83/04* | (2006.01) |
| *H04R 17/00* | (2006.01) |
| *G10K 11/30* | (2006.01) |
| *H04R 19/00* | (2006.01) |
| *C08G 77/20* | (2006.01) |
| *C08G 77/12* | (2006.01) |
| *C08G 77/00* | (2006.01) |

(52) U.S. Cl.
CPC ............ *A61B 5/0095* (2013.01); *C08L 83/04* (2013.01); *H04R 17/00* (2013.01); *C08G 77/12* (2013.01); *C08G 77/20* (2013.01); *C08G 77/80* (2013.01); *G10K 11/30* (2013.01); *H04R 19/00* (2013.01)

(58) Field of Classification Search
CPC ........ A61B 5/0095; A61B 8/13; C08G 77/12; C08G 77/20; C08G 77/80; C08L 83/04; G10K 11/30; H04R 17/00; H04R 19/00
See application file for complete search history.

(56) References Cited

U.S. PATENT DOCUMENTS

| | | | |
|---|---|---|---|
| 2002/0006079 A1 | 1/2002 | Saito et al. | |
| 2016/0051228 A1* | 2/2016 | Nakai | A61B 8/4444 600/407 |
| 2017/0252465 A1* | 9/2017 | Nagai | C08L 83/04 |
| 2018/0344287 A1* | 12/2018 | Nakai | H04R 17/00 |

FOREIGN PATENT DOCUMENTS

| | | | | |
|---|---|---|---|---|
| JP | 62-89765 A | 4/1987 | | |
| JP | 8-305375 A | 11/1996 | | |
| JP | 2016-107075 A | 6/2016 | | |
| WO | 2016/088699 A1 | 6/2016 | | |
| WO | WO-2016088699 A1 * | 6/2016 | ........... | A61B 5/0095 |
| WO | WO-2017130890 A1 * | 8/2017 | ........... | A61B 5/0095 |

OTHER PUBLICATIONS

Gelest, DMS-V31S15 Safety Data Sheet, retrieved from the internet at <https://www.gelest.com/wp-content/uploads/DMS-V31S15_VINYL-TERMINATED-POLYDIMETHYLSILOXANE-FUMED-SILICA-REINFORCED_GHS-US_English-US.pdf> on Sep. 12, 2022. (Year: 2016).*
International Search Report dated Dec. 5, 2017 from the International Bureau in counterpart International Application No. PCT/JP2017/033325.
International Preliminary Report on Patentability dated Feb. 1, 2019 from the International Bureau in counterpart International Application No. PCT/JP2017/033325.
Written Opinion dated Dec. 5, 2017 from the International Bureau in counterpart International Application No. PCT/JP2017/033325.
Communication dated Sep. 11, 2019, from the European Patent Office in counterpart European Application No. 17852951.7.
Office Action dated Dec. 21, 2022 issued by the European Patent Office in European Application No. 17 852 951.7.

* cited by examiner

*Primary Examiner* — James C Goloboy
(74) *Attorney, Agent, or Firm* — Sughrue Mion, PLLC

(57) ABSTRACT

Provided are a composition for an acoustic wave probe which includes polysiloxane that has a vinyl group and a phenyl group, polysiloxane that has two or more Si—H groups in a molecular chain, a titanium oxide particle, and a silica particle, in which at least one of the titanium oxide particle (C) or the silica particle (D) is a particle subjected to surface treatment; a silicone resin for an acoustic wave probe; an acoustic wave probe; an acoustic wave measurement apparatus; an ultrasound diagnostic apparatus; an ultrasound probe; a photoacoustic wave measurement apparatus; and an ultrasound endoscope.

19 Claims, 1 Drawing Sheet

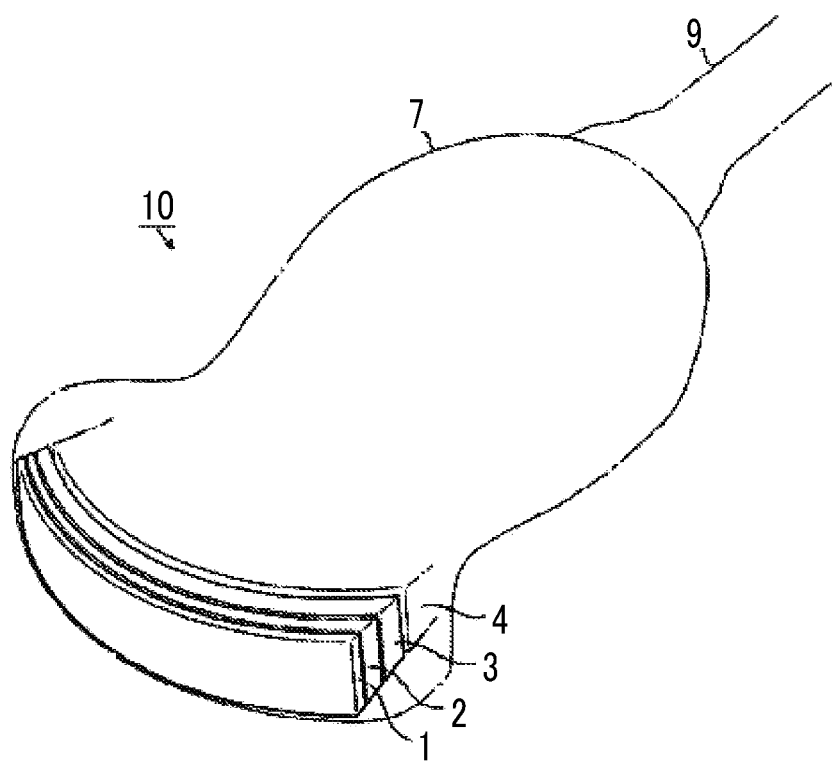

COMPOSITION FOR ACOUSTIC WAVE PROBE, SILICONE RESIN FOR ACOUSTIC WAVE PROBE FORMED OF THE SAME, ACOUSTIC WAVE PROBE, ULTRASOUND PROBE, ACOUSTIC WAVE MEASUREMENT APPARATUS, ULTRASOUND DIAGNOSTIC APPARATUS, PHOTOACOUSTIC WAVE MEASUREMENT APPARATUS, AND ULTRASOUND ENDOSCOPE

CROSS-REFERENCE TO RELATED APPLICATIONS

This application is a Continuation of PCT International Application No. PCT/JP2017/033325 filed on Sep. 14, 2017, which claims priority under 35 U.S.C. § 119 (a) to Japanese Patent Application No. 2016-183062 filed in Japan on Sep. 20, 2016. Each of the above applications is hereby expressly incorporated by reference, in its entirety, into the present application.

BACKGROUND OF THE INVENTION

1. Field of the Invention

The present invention relates to a composition for an acoustic wave probe, a silicone resin for an acoustic wave probe formed of the same, an acoustic wave probe, and an ultrasound probe. Furthermore, the present invention relates to an acoustic wave measurement apparatus, an ultrasound diagnostic apparatus, a photoacoustic wave measurement apparatus, and an ultrasound endoscope.

2. Description of the Related Art

In an acoustic wave measurement apparatus, an acoustic wave probe is used which irradiates a test object or a site (hereinafter, simply referred to as a subject) with an acoustic wave, receives a reflected wave (echo) thereof, and outputs a signal. An electrical signal converted from the reflected wave which has been received by this acoustic wave probe is displayed as an image. Accordingly, the interior of the test object is visualized and observed.

Acoustic waves, such as ultrasonic waves and photoacoustic waves, which have an appropriate frequency in accordance with a test object and/or measurement conditions, are selected as the acoustic waves.

For example, an ultrasound diagnostic apparatus transmits an ultrasonic wave to the interior of a test object, receives the ultrasonic wave reflected by the tissues inside the test object, and displays the received ultrasonic wave as an image. A photoacoustic wave measurement apparatus receives an acoustic wave radiated from the interior of a test object due to a photoacoustic effect, and displays the received acoustic wave as an image. The photoacoustic effect is a phenomenon in which an acoustic wave (typically an ultrasonic wave) is generated through thermal expansion after a test object absorbs an electromagnetic wave and generates heat in a case where the test object is irradiated with an electromagnetic wave pulse of visible light, near infrared light, microwave, or the like.

An acoustic wave measurement apparatus performs transmission and reception of an acoustic wave on a living body (typically, the human body) which is a test object. Therefore, it is necessary to fulfill requirements such as consistency in the acoustic impedance within the living body (typically a human body) and/or a decrease in acoustic attenuation.

For example, a probe for an ultrasound diagnostic apparatus (also referred to as an ultrasound probe) which is a kind of acoustic wave probe comprises a piezoelectric element which transmits and receives an ultrasonic wave and an acoustic lens which is a portion coming into contact with a living body. An ultrasonic wave oscillating from the piezoelectric element is incident on the living body after being transmitted through the acoustic lens. In a case where the difference between acoustic impedance (density×acoustic velocity) of the acoustic lens and acoustic impedance of the living body is large, the ultrasonic wave is reflected by the surface of the living body. Therefore, the ultrasonic wave is not efficiently incident on the living body. For this reason, it is difficult to obtain a favorable resolution. In addition, it is desirable that ultrasonic attenuation of the acoustic lens is low in order to transmit and receive the ultrasonic wave with high sensitivity.

For this reason, a silicone resin of which the acoustic impedance is close to the acoustic impedance of a living body (in the case of a human body, $1.40 \times 10^6$ to $1.70 \times 10^6$ $kg/m^2/sec$) and which has a low ultrasonic attenuation is used as a material of the acoustic lens.

For example, JP2016-107075A discloses a composition for an acoustic wave probe which includes a polysiloxane mixture containing polysiloxane having a vinyl group, polysiloxane having two or more Si—H's in a molecular chain, and inorganic compound particles having a particular particle diameter and specific weight. JP2016-107075A discloses that an acoustic wave probe is formed using a silicone resin obtained by vulcanizing this resin composition, thereby suppressing acoustic attenuation or improving mechanical characteristics.

SUMMARY OF THE INVENTION

The invention disclosed in JP2016-107075A is an invention for improving characteristics in which the acoustic attenuation is decreased according to the acoustic impedance of the acoustic wave probe which is set within a predetermined numerical value range, or the resin hardness is improved so that the mechanical strength is also improved; which are required for an acoustic wave probe used for a living body. However, recently, further improvement in performance of the acoustic wave probe has been required for further improvement in sensitivity or accuracy of diagnosis. Among these, improvement in photoreflectance of the acoustic wave probe has been strongly required so that a signal from the acoustic wave probe to a measurement apparatus is not affected by irradiation light in a case where a subject is irradiated with light in photoacoustic wave measurement in which a sound generated from the subject is measured to be imaged. Furthermore, from a viewpoint of long-term use, and the necessity for resistance to powerful antiseptics, improvement in chemical resistance has been strongly required.

In view of the above-described circumstances, an object of the present invention is to provide a composition for an acoustic wave probe which is capable of realizing an acoustic impedance value close to that of a living body, or realizing a decrease in the acoustic attenuation and improvement in the resin hardness and the tear strength, and further realizing improvement in photoreflectance and chemical resistance in a silicone resin for an acoustic wave probe (hereinafter simply referred to as "silicone resin"). In addition, another object of the present invention is to provide a silicone resin for an acoustic wave probe formed of this composition for an acoustic wave probe; an acoustic wave probe formed of this silicone resin for an acoustic wave probe; and an acoustic wave measurement apparatus and an ultrasound diagnostic apparatus formed of this acoustic wave probe. Furthermore, still another object of the present invention is to provide a photoacoustic wave measurement apparatus and an ultrasound endoscope formed of the above-described silicone resin for an acoustic wave probe.

Furthermore, still another object of the present invention is to provide an ultrasound probe comprising a capacitive micromachined ultrasonic transducer (cMUT) as an ultrasonic transducer array, and an acoustic lens made of the above-described silicone resin for an acoustic wave probe.

As a result of intensive studies on a composition that can be used for producing an acoustic wave probe, the inventors of the present invention have found that above-described problems are solved by a composition containing two specific types of polysiloxane, titanium oxide particle, and silica particles, in which the titanium oxide particles and/or the silica particles are subjected to surface treatment, and therefore have completed the present invention based on these findings.

The above-described problems are solved by the following means.

<1> A composition for an acoustic wave probe, comprising:
polysiloxane (A) that has a vinyl group and a phenyl group;
polysiloxane (B) that has two or more Si—H groups in a molecular chain;
a titanium oxide particle (C); and
a silica particle (D),
in which at least one of the titanium oxide particle (C) or the silica particle (D) is a particle subjected to surface treatment.

<2> The composition for an acoustic wave probe according to <1>, in which 0.1 to 60 parts by mass in total of the component (C) and the component (D) are contained in 100 parts by mass in total of the components (A) to (D).

<3> The composition for an acoustic wave probe according to <1> or <2>, in which 10 to 99.4 parts by mass of the component (A) and 0.5 to 90 parts by mass of the component (B) are contained in 100 parts by mass in total of the components (A) to (D).

<4> The composition for an acoustic wave probe according to any one of <1> to <3>, in which an average primary particle diameter of the component (C) is 100 to 300 nm.

<5> The composition for an acoustic wave probe according to any one of <1> to <4>, in which the component (C) is a particle subjected to surface treatment using a silicon compound.

<6> The composition for an acoustic wave probe according to any one of <1> to <5>, in which the component (D) is a particle subjected to surface treatment using a silicon compound.

<7> The composition for an acoustic wave probe according to <6>, in which the component (D) is a particle subjected to surface treatment using a silane compound.

<8> The composition for an acoustic wave probe according to <7>, in which the component (D) is a particle subjected to surface treatment using a trimethylsilylating agent.

<9> The composition for an acoustic wave probe according to any one of <6> to <8>, in which a degree of methanol hydrophobicity of the component (D) subjected to surface treatment is 40% to 80% by mass.

<10> The composition for an acoustic wave probe according to any one of <6> to <9>, in which the component (D) subjected to surface treatment is truly spherical.

<11> The composition for an acoustic wave probe according to any one of <1> to <10>, in which a mass average molecular weight of the component (A) is from 20,000 to 200,000.

<12> The composition for an acoustic wave probe according to <11>, in which the mass average molecular weight of the component (A) is from 40,000 to 150,000.

<13> The composition for an acoustic wave probe according to any one of <1> to <12>, in which the component (B) is a compound containing a phenyl group.

<14> The composition for an acoustic wave probe according to any one of <1> to <13>, further comprising 0.00001 to 0.01 parts by mass of platinum or a platinum compound with respect to 100 parts by mass in total of the components (A) to (D).

<15> A silicone resin for an acoustic wave probe which is obtained by vulcanizing the composition for an acoustic wave probe according to any one of <1> to <14>.

<16> An acoustic wave probe comprising an acoustic lens and/or an acoustic matching layer made of the silicone resin for an acoustic wave probe according to <15>.

<17> An ultrasound probe comprising a capacitive micromachined ultrasonic transducer as an ultrasonic transducer array; and an acoustic lens made of the silicone resin for an acoustic wave probe according to <15>.

<18> An acoustic wave measurement apparatus comprising the acoustic wave probe according to <16>.

<19> An ultrasound diagnostic apparatus comprising the acoustic wave probe according to <16>.

<20> A photoacoustic wave measurement apparatus comprising an acoustic lens made of the silicone resin for an acoustic wave probe according to <15>.

<21> An ultrasound endoscope comprising an acoustic lens made of the silicone resin for an acoustic wave probe according to <15>.

Unless otherwise specified in the description of the present specification, in a case where there are groups having a plurality of the same reference numerals as each other in general formulae representing compounds, these may be the same as or different from each other, and a group (for example, an alkyl group) specified by each group may further have a substituent. In addition, the "Si—H group" means a group having three bonds on a silicon atom, but the description of the bonds is not repeated and the notation is simplified.

In addition, in the present specification. "to" means a range including numerical values denoted before and after "to" as a lower limit value and an upper limit value.

Unless otherwise specified, the mass average molecular weight in the present specification refers to a value (in terms of polystyrene) measured through gel permeation chromatography (GPC).

The above-described characteristics and advantages and other characteristics and advantages of the present invention become clearer in the following descriptions with reference to the accompanying drawing.

By vulcanizing the composition for an acoustic wave probe of the present invention, it is possible to provide the silicone resin for an acoustic wave probe which is capable of realizing an acoustic impedance value close to that of a living body, or realizing a decrease in the acoustic attenuation and improvement in the resin hardness and the tear strength, and further realizing improvement in photoreflectance and chemical resistance. In addition, the silicone resin for an acoustic wave probe of the present invention has the acoustic impedance value close to that of the living body and has low acoustic attenuation, and is excellent in the resin hardness, tear strength, photoreflectance, and chemical resistance. Furthermore, according to the present invention, it is possible to provide the acoustic wave probe, the acoustic wave measurement apparatus, and the ultrasound diagnostic apparatus, which are formed of the silicone resin for an acoustic wave probe which exhibits excellent effects as described above. Furthermore, according to the present invention, it is possible to provide the photoacoustic wave measurement apparatus and the ultrasound endoscope, which are formed of the silicone resin for an acoustic wave probe which exhibits excellent effects as described above.

Furthermore, according to the present invention, it is possible to provide the ultrasound probe comprising cMUT as the ultrasonic transducer array; and the acoustic lens made of the above-described silicone resin for an acoustic wave probe.

BRIEF DESCRIPTION OF THE DRAWINGS

FIG. 1 is a perspective transparent view of an example of a convex ultrasound probe which is an embodiment of an acoustic wave probe.

DESCRIPTION OF THE PREFERRED EMBODIMENTS

<Composition for Acoustic Wave Probe>

A composition for an acoustic wave probe of the embodiment of the present invention (hereinafter simply referred to as "composition") includes at least polysiloxane (A) having a vinyl group and a phenyl group; polysiloxane (B) having two or more Si—H groups in a molecular chain; a titanium oxide particle (C); and a silica particle (D) (hereinafter, the components (A) to (D) in the composition will be collectively referred to as "polysiloxane mixture" or "polysiloxane homogeneous mixture"). In this composition, the titanium oxide particle (C) and/or the silica particle (D) are subjected to surface treatment.

Hereinafter, each component contained in the composition of the embodiment of the present invention may be referred to without attaching the signs. For example, the titanium oxide particle (C) will be simply referred to as "titanium oxide particle."

As described above, the polysiloxane mixture used in the present invention contains the polysiloxane (polyorganosiloxane) (A) having a vinyl group and a phenyl group; and the polysiloxane (B) having two or more Si—H groups in a molecular chain. However, the polysiloxane (B) having two or more Si—H groups in a molecular chain is preferably polyorganosiloxane (B) having two or more Si—H groups in a molecular chain.

The polysiloxane (A) having a vinyl group and a phenyl group, the polysiloxane (B) having two or more Si—H groups in a molecular chain, the titanium oxide particle, and the silica will be described in this order in the following detailed description. The present invention is not limited to the embodiment described below.

<Polysiloxane (A) Having Vinyl Group and Phenyl Group>

The polysiloxane (A) having a vinyl group and a phenyl group (hereinafter, simply referred to as polysiloxane (A)) which is used in the present invention has two or more vinyl groups in a molecular chain.

Examples of the polysiloxane (A) having a vinyl group and a phenyl group include polysiloxane (a) having vinyl groups at least at both terminals of a molecular chain (hereinafter, simply referred to as polysiloxane (a)), or polysiloxane (b) having at least two —O—Si(CH$_3$)$_2$(CH=CH$_2$) in a molecular chain (hereinafter, simply referred to as polysiloxane (b)). Among them, the polysiloxane (a) having vinyl groups at least at both terminals of a molecular chain is preferable.

The polysiloxane (a) is preferably linear and the polysiloxane (b) is preferably polysiloxane (b) in which —O—Si(CH$_3$)$_2$(CH=CH$_2$) is bonded to a Si atom constituting a main chain.

The polysiloxane (A) having a vinyl group and a phenyl group is subjected to hydrosilylation through a reaction with the polysiloxane (B) having two or more Si—H groups in the presence of a platinum catalyst. A cross-linked structure is formed through this hydrosilylation reaction (addition vulcanizing reaction).

A content of the vinyl group of the polysiloxane (A) is not particularly limited. The content of the vinyl group is, for example, 0.01 to 5 mol % and preferably 0.05 to 2 mol % from the viewpoint of forming a sufficient network between each of the components contained in the composition for an acoustic wave probe.

In addition, a content of the phenyl group of the polysiloxane (A) is not particularly limited. The content of the phenyl group is, for example, 1 to 80 mol % and preferably 2 to 40 mol % from the viewpoint of mechanical strength in a case where a silicone resin for an acoustic wave probe is made.

The content of the vinyl group referred to herein is represented by mol % of the vinyl group-containing siloxane unit based on 100 mol % of all the units constituting the polysiloxane (A), and in a case where all Si atoms of a Si—O unit constituting a main chain and Si at a terminal are substituted by at least one vinyl group, the content becomes 100 mol %.

Similarly, the content of the phenyl group is represented by mol % of the phenyl group-containing siloxane unit based on 100 mol % of all the units constituting the polysiloxane (A), and in a case where all Si atoms of Si in a Si—O unit and at a terminal which constitute a main chain all Si atoms of the Si—O unit constituting the main chain and Si at the terminal are substituted by at least one phenyl group, the content becomes 100 mol %.

The "unit" of the polysiloxane refers to the Si—O unit constituting the main chain and Si at the terminal.

A degree of polymerization and a specific gravity are not particularly limited. The degree of polymerization is preferably 200 to 3,000 and more preferably 400 to 2,000, and the specific gravity is preferably 0.9 to 1.1 from the viewpoint of improving mechanical strength, hardness, chemical stability, and the like of an obtained silicone resin for an acoustic wave probe.

A mass average molecular weight of the polysiloxane (A) having the vinyl group and the phenyl group is not particularly limited, but a lower limit thereof is preferably 10,000 or more, more preferably 20,000 or more, even more preferably 30,000 or more, and particularly preferably 40,000 or more, from the viewpoints of the mechanical strength, the hardness, and easiness of processing. An upper limit is preferably 300,000 or less, more preferably 200,000 or less, even more preferably 150,000 or less, and particularly preferably 120,000 or less.

The mass average molecular weight can be measured by, for example, preparing a GPC apparatus HLC-8220 (trade name, manufactured by TOSOH CORPORATION), using TOLUENE (manufactured by Shonan Wako Junyaku K.K.) as an eluent, using TSKgel (registered trademark), G3000HXL+TSKgel (registered trademark), and G2000HXL (all of which are trade names) as columns, and using a RI detector under conditions of a temperature of 23° C. and a flow rate of 1 mL/min.

A kinematic viscosity at 25° C. is preferably $1\times10^{-5}$ to 10 $m^2/s$, more preferably $1\times10^{-4}$ to 1 $m^2/s$, and even more preferably $1\times10^{-3}$ to 0.5 $m^2/s$.

The kinematic viscosity can be measured and obtained at a temperature of 23° C. using a Ubbelohde-type viscometer (for example, a trade name of SU manufactured by SIBATA SCIENTIFIC TECHNOLOGY LTD.) in compliance with JIS Z8803.

Polysiloxane represented by General Formula (A) is preferable the polysiloxane (a) having vinyl groups at least at both terminals of a molecular chain.

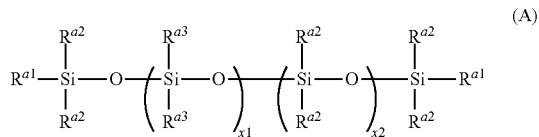

In General Formula (A), $R^{a1}$ represents a vinyl group and $R^{a2}$ and $R^{a3}$ each independently represent an alkyl group, a cycloalkyl group, an alkenyl group, or a phenyl group. x1 and x2 each independently represent an integer of 1 or more. Here, each of a plurality of $R^{a2}$'s, and each of a plurality of $R^{a3}$'s may be the same as or different from each other, and at least one thereof represents a phenyl group. In addition, each of the groups of $R^{a2}$ and $R^{a3}$ may be substituted by a substituent.

The number of carbon atoms in an alkyl group in $R^{a2}$ and $R^{a3}$ is preferably 1 to 10, more preferably 1 to 4, even more preferably 1 or 2, and particularly preferably 1. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

The number of carbon atoms in a cycloalkyl group in $R^{a2}$ and $R^{a3}$ is preferably 3 to 10, more preferably 5 to 10, and even more preferably 5 or 6. In addition, the cycloalkyl group is preferably a 3-membered ring, a 5-membered ring, or a 6-membered ring, and more preferably a 5-membered ring or a 6-membered ring. Examples of the cycloalkyl group include a cyclopropyl group, a cyclopentyl group, and a cyclohexyl group.

The number of carbon atoms in an alkenyl group in $R^{a2}$ and $R^{a3}$ is preferably 2 to 10, more preferably 2 to 4, and even more preferably 2. Examples of the alkenyl group include a vinyl group, an allyl group, and a butenyl group.

The alkyl group, the cycloalkyl group, the alkenyl group, and the phenyl group may have a substituent. Examples of such a substituent include a halogen atom, an alkyl group, a cycloalkyl group, an alkenyl group, an aryl group, an alkoxy group, an aryloxy group, an alkylthio group, an arylthio group, a silyl group, and a cyano group.

Examples of the group having a substituent include a halogenated alkyl group.

$R^{a2}$ and $R^{a3}$ are preferably an alkyl group, an alkenyl group, or a phenyl group, more preferably an alkyl group having 1 to 4 carbon atoms, a vinyl group, or a phenyl group, and even more preferably a methyl group, a vinyl group, or a phenyl group.

Among them, $R^{a2}$ is preferably a methyl group, and $R^{a3}$ is preferably a phenyl group. In addition, it is preferable that both $R^{a3}$'s in the repetition of x1 are phenyl groups.

x1 is preferably an integer of 1 to 3,000, and more preferably an integer of 5 to 1.000.

x2 is preferably an integer of 1 to 3,000, and more preferably an integer of 40 to 1,000.

In the present invention, each of repeating units "—Si$(R^{a3})_2$—O—" and "—Si$(R^{a2})_2$—O—" in General Formula (A) may exist in a block polymerized form, or may be in a form existing randomly.

Specific examples of the polysiloxane (A) include PDV series (trade name) manufactured by GELEST, INC. (for example, PDV-0341, PDV-0346. PDV-0535, PDV-0541, PDV-1631, PDV-1635, PDV-1641, PDV-2335, PMV-9925, PVV-3522, FMV-4031, and EDV-2022).

The polysiloxane (A) having the vinyl group and the phenyl group in the embodiment of the present invention may be used singly or in a combination of two or more kinds thereof.

<Polysiloxane (B) Having Two or More Si—H Groups in Molecular Chain>

The polysiloxane (B) having two or more Si—H groups in a molecular chain used in the present invention (hereinafter, simply referred to as polysiloxane (B)) has two or more Si—H groups in a molecular chain. In a case where the polysiloxane (B) has a "—SiH$_2$—" structure, the number of the Si—H groups in the "—SiH$_2$—" structure is 2. In addition, in a case where the polysiloxane (B) has a "—SiH$_3$—" structure, the number of the Si—H groups in the "—SiH$_3$—" structure is 3.

In a case where two or more Si—H groups are present in a molecular chain, it is possible to crosslink polysiloxane having at least two polymerizable unsaturated groups.

In the polysiloxane (B), a linear structure and a branched structure are present, and the linear structure is preferable.

The mass average molecular weight of the linear structure is preferably 500 to 50,000 and more preferably 1,000 to 10,000 from the viewpoints of the mechanical strength and the hardness.

In addition, the polysiloxane (B) preferably has a phenyl group, and a content of the phenyl group is not particularly limited. The content of the phenyl group is, for example, 20 to 80 mol % and preferably 30 to 70 mol % from the viewpoint of mechanical strength in a case where a silicone resin for an acoustic wave probe is made.

The content of the phenyl group referred to herein is a content calculated by replacing the polysiloxane (A) with the polysiloxane (B) in the content of the phenyl group in the polysiloxane (A).

An Si—H equivalent of the polysiloxane (B) is preferably 1,300 g/mol or less and more preferably 500 g/mol or less. In addition, this Si—H equivalent is preferably 50 g/mol or more and more preferably 100 g/mol or more.

In the present invention, a condition in which both polysiloxane (A) and polysiloxane (B) have the phenyl group is preferable for improving compatibility.

The silicone resin for an acoustic wave probe of the embodiment of the present invention has a bulky phenyl group, thereby increasing an acoustic velocity and increasing the hardness and the specific gravity. Therefore, the acoustic impedance can be improved.

The polysiloxane (B) which has a linear structure and two or more Si—H groups in a molecular chain is preferably polysiloxane represented by General Formula (B).

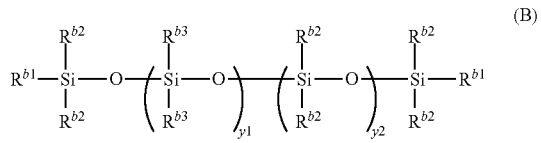

In General Formula (B), $R^{b1}$ and $R^{b2}$ each independently represent a hydrogen atom, an alkyl group, a cycloalkyl group, an aryl group, or —O—Si$(R^{b6})_2(R^{b5})$. $R^{b5}$ and $R^{b6}$ each independently represent a hydrogen atom, an alkyl group, a cycloalkyl group, or an aryl group. $R^{b3}$ and $R^{b4}$ each independently represent a hydrogen atom, an alkyl group, a cycloalkyl group, an alkenyl group, an aryl group, or —O—Si$(R^{b8})_2(R^{b7})$. $R^{b7}$ and $R^{b8}$ each independently represent a hydrogen atom, an alkyl group, a cycloalkyl group, an alkenyl group, or an aryl group. y1 represents an integer of 1 or more, and y2 represents an integer of 0 or more. Here, each of a plurality of $R^{b1}$'s, and each of a plurality of $R^{b2}$'s may be the same as or different from each other. In addition, in a case where a plurality of $R^{b3}$'s to $R^{b8}$'s are present, each of a plurality of $R^{b3}$'s, a plurality of $R^{b4}$'s, a plurality of $R^{b5}$'s, a plurality of $R^{b6}$'s, a plurality of $R^{b7}$'s, and a plurality of $R^{b8}$'s may be the same as or different from each other, or each of the groups of $R^{b1}$ to $R^{b8}$ may further be substituted by a substituent. However, two or more Si—H groups are present in a molecular chain.

An alkyl group and a cycloalkyl group in $R^{b1}$ and $R^{b2}$ are the same as an alkyl group and a cycloalkyl group in $R^{a2}$ and $R^{a3}$, and preferred ranges thereof are also the same as each other. An alkyl group, a cycloalkyl group, and an alkenyl group in $R^{b3}$ and $R^{b4}$ are the same as an alkyl group, a cycloalkyl group, and an alkenyl group in $R^{a2}$ and $R^{a3}$, and preferred ranges thereof are also the same as each other. The number of carbon atoms in an aryl group in $R^{b1}$ to $R^{b4}$ is preferably 6 to 12, more preferably 6 to 10, and even more preferably 6 to 8. Examples of the aryl group include a phenyl group, a tolyl group, and a naphthyl group.

An alkyl group, a cycloalkyl group, and an aryl group in $R^{b5}$ and $R^{b6}$ of —O—Si$(R^{b6})_2(R^{b5})$ are synonymous with an alkyl group, a cycloalkyl group, and an aryl group in $R^{b1}$ and $R^{b2}$, and preferred ranges thereof are also the same as each other.

An alkyl group, a cycloalkyl group, an alkenyl group, and an aryl group in $R^{b7}$ and $R^{b8}$ of —O—Si$(R^{b6})_2(R^{b7})$ are synonymous with an alkyl group, a cycloalkyl group, an alkenyl group, and an aryl group in $R^{b3}$ and $R^{b4}$, and preferred ranges thereof are also the same as each other.

$R^{b1}$ and $R^{b2}$ are preferably a hydrogen atom, an alkyl group, an aryl group, or —O—Si$(R^{b6})_2(R^{b5})$, and more preferably a hydrogen atom, an alkyl group having 1 to 4 carbon atoms, a phenyl group, or —O—Si$(CH_3)_2H$.

$R^{b3}$ and $R^{b4}$ are preferably a hydrogen atom, an alkyl group, an alkenyl group, an aryl group, or —O—Si$(R^{b8})_2(R^{b7})$, and more preferably a hydrogen atom, an alkyl group having 1 to 4 carbon atoms, a vinyl group, a phenyl group, or —O—Si$(CH_3)_2H$.

Among them, $R^{b1}$ and $R^{b2}$ are preferably a hydrogen atom, an alkyl group, or an aryl group, more preferably a hydrogen atom or an alkyl group, and even more preferably a hydrogen atom or a methyl group. In addition, a combination in which $R^{b1}$ is a hydrogen atom and $R^{b2}$ is a methyl group is preferable.

$R^{b3}$ is preferably a hydrogen atom, an alkyl group, an alkenyl group, an aryl group, or —O—Si$(R^{b8})(R^{b7})$, more preferably a hydrogen atom or an alkyl group, and particularly preferably a hydrogen atom.

$R^{b4}$ is preferably a hydrogen atom, an alkyl group, an alkenyl group, an aryl group, or —O—Si$(R^{b7})_2(R^{b7})$, more preferably a hydrogen atom, an alkyl group, or an aryl group, even more preferably a hydrogen atom, a methyl group, or a phenyl group, still more preferably a methyl group or a phenyl group, and particularly preferably a phenyl group.

y2 is preferably an integer of 1 or more.

y1+y2 is preferably an integer of 5 to 2,000, more preferably an integer of 7 to 1,000, even more preferably an integer of 10 to 50, and particularly preferably an integer of 15 to 30.

In the present invention, each of repeating units "—Si$(R^{b2})(R^{b3})$—O—" and "—Si$(R^{b2})(R^{b4})$—O—" in General Formula (B) may exist in a block polymerized form in polysiloxane, or may be in a form existing randomly.

As a combination of $R^{b1}$ to $R^{b4}$, a combination in which $R^{b1}$ is a hydrogen atom or an alkyl group having 1 to 4 carbon atoms, $R^{b2}$ is an alkyl group having 1 to 4 carbon atoms, $R^{b3}$ is a hydrogen atom, and $R^{b4}$ is a hydrogen atom or a phenyl group, is preferable.

Examples of the polysiloxane (B) with a linear structure include HMS-151 (Si—H equivalent of 490 g/mol), HMS-301 (Si—H equivalent of 245 g/mol), HMS-501 (Si—H equivalent of 135 g/mol), and HMS-064 (Si—H equivalent of 1,240 g/mol) as methylhydrosiloxane-dimethylsiloxane copolymers (trimethylsiloxy terminated); HMS-991 (Si—H equivalent of 67 g/mol) as a methylhydrosiloxane polymer (trimethylsiloxy terminated); and HPM-502 (Si—H equivalent of 165 g/mol) as a methylhydrosiloxane-phenylmethylsiloxane copolymer (hydride terminated) (all of which are trade names of GELEST, INC.).

It is preferable that both the linear structure and the branched structure have no vinyl group from the viewpoint of preventing the progress of a cross-linking reaction within a molecule. Among these, it is preferable that the branched structure has no vinyl group.

The polysiloxane (B), which has a branched structure and two or more Si—H groups in a molecular chain, has a branched structure and two or more hydrosilyl groups (Si—H groups).

A specific gravity is preferably 0.9 to 0.95.

The polysiloxane (B) with a branched structure is preferably represented by Average Composition Formula (b).

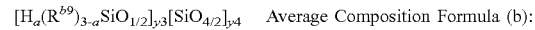   Average Composition Formula (b):

Here, $R^{b9}$ represents an alkyl group, a cycloalkyl group, an alkenyl group, or an aryl group, a represents 0.1 to 3, and y3 and y4 each independently represent an integer of 1 or more.

An alkyl group, a cycloalkyl group, an alkenyl group, and an aryl group in $R^{b9}$ are synonymous with an alkyl group, a cycloalkyl group, an alkenyl group, and an aryl group in $R^{b3}$ and $R^{b4}$, and preferred ranges thereof are also the same as each other.

a is preferably 1.

A content rate of a hydrosilyl group represented by a/3 is preferably greater than 0.1 and less than 0.6 and more preferably greater than 0.1 and less than 0.4.

In contrast, in a case of representing the polysiloxane (B) with a branched structure using a chemical structural formula, polysiloxane in which —O—Si(CH$_3$)$_2$(H) is bonded to a Si atom constituting a main chain is preferable, and polysiloxane having a structure represented by General Formula (Bb) is more preferable.

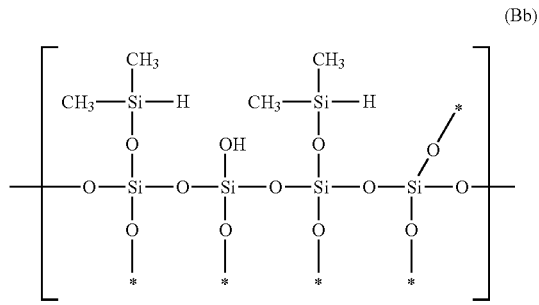

In General Formula (Bb), * means a bond with at least a Si atom of siloxane.

Examples of the polysiloxane (B) with a branched structure include HQM-107 (trade name of Hydride Q Resin manufactured by GELEST, INC.) and HDP-111 (trade name of polyphenyl-(dimethylhydroxy)siloxane (hydride terminated), [(HMe$_2$SiO)(C$_6$H$_5$Si)O]: 99 to 100 mol % manufactured by GELEST, INC.).

Me is CH$_3$.

The polysiloxane (B) having two or more Si—H groups in a molecular chain in the embodiment of the present invention may be used singly, or in a combination of two or more kinds thereof. In addition, the polysiloxane (B) with a linear structure and the polysiloxane (B) with a branched structure may be used in combination.

A total content of the titanium oxide particles and silica particles in 100 parts by mass of the polysiloxane mixture used in the present invention is not particularly limited, but a lower limit is preferably 0.1 parts by mass or more, more preferably 1 part by mass or more, even more preferably 5 parts by mass or more, still more preferably 10 parts by mass or more, and particularly preferably 20 parts by mass or more. An upper limit is preferably 70 parts by mass or less, more preferably 60 parts by mass or less, even more preferably 55 parts by mass or less, and particularly preferably 50 parts by mass or less.

In a case where the contents of the titanium oxide particles and the silica particles are within the above-described ranges, it is possible that an acoustic impedance value becomes close to that of a living body, thereby improving the tear strength, and increasing acoustic sensitivity, with more efficiency.

In addition, a content of the polysiloxane having the vinyl group and the phenyl group in 100 parts by mass in total of the polysiloxane mixture is preferably 10 to 99.4 parts by mass, more preferably 10 to 89.9 parts by mass. A lower limit of the content of the polysiloxane having two or more Si—H groups in a molecular chain is preferably 0.1 parts by mass or more, more preferably 0.2 parts by mass or more, and particularly preferably 0.5 parts by mass or more. An upper limit thereof is preferably 90 parts by mass or less and more preferably 70 parts by mass or less. The content of the polysiloxane having the vinyl group and the phenyl group is more preferably 30 to 80 parts by mass, and the content of the polysiloxane having two or more Si—H groups in a molecular chain is even more preferably 0.5 to 50 parts by mass. In a case where the content of the polysiloxane having the vinyl group and the phenyl group and the content of the polysiloxane having two or more Si—H groups in a molecular chain are within in the above-described ranges, a vulcanizing reaction can be appropriately performed, thereby increasing the JIS hardness and the tear strength.

The polysiloxane homogeneous mixture refers to a mixture which does not contain a catalyst for crosslinking and polymerizing the polysiloxane having the vinyl group and the phenyl group, and the polysiloxane having two or more Si—H groups in a molecular chain. Accordingly, the titanium oxide particles which are not a catalyst are contained in the polysiloxane homogeneous mixture.

<Titanium Oxide Particle (C)>

The composition for an acoustic wave probe of the embodiment of the present invention contains the titanium oxide particles. By the titanium oxide particles contained in the composition, the acoustic impedance of the silicone resin for an acoustic wave probe of the embodiment of the present invention, which is obtained by vulcanizing the composition for an acoustic wave probe, can be improved. In addition, the titanium oxide particles have a high degree of light scattering properties, and thus are capable of improving the photoreflectance of the silicone resin for an acoustic wave probe of the embodiment of the present invention. Furthermore, as described later, by the titanium oxide particles contained in the composition for an acoustic wave probe of the embodiment of the present invention in combination with the silica particles, the chemical resistance of the silicone resin for an acoustic wave probe of the embodiment of the present invention can be improved.

An average primary particle diameter of the titanium oxide particles used in the present invention is not particularly limited, but is preferably 10 nm to 500 nm, more preferably 50 nm to 420 nm, and particularly preferably 100 nm to less than 300 nm.

With the average primary particle diameter of the titanium oxide particles used in the present invention within the above-described ranges, in a case where mechanical stress is applied to the silicone resin for an acoustic wave probe, it is considered that the silicone resin is more likely to exert a function thereof as a stopper.

As a result, it is considered that the acoustic impedance is more increased, thereby effectively suppressing an increase in the acoustic attenuation, and the hardness and the mechanical strength (tear strength) of the silicone resin for an acoustic wave probe is more improved.

The average primary particle diameter is described in the catalog of the manufacturer of the titanium oxide particles. However, an average primary particle diameter of titanium oxide particles whose average primary particle diameter is not described in the catalog or titanium oxide particles which are newly produced, can be obtained by averaging particle diameters measured by transmission electron microscopy (TEM). That is, with respect to one particle of an electron micrograph captured by TEM, a short diameter and a long diameter are measured, and an average value thereof is obtained as a particle diameter of one particle. In the present invention, particle diameters of 300 randomly selected particles are averaged to obtain the average primary particle diameter.

In addition, in a case where the titanium oxide particles are subjected to surface treatment to be described later, the average primary particle diameter means an average primary particle diameter of the titanium oxide particles in the surface-treated state.

Commercially available titanium oxide particles can be used, and examples thereof include TITONE (registered trademark) R-24, TITONE R-45M, TITONE R-38L, R-3 L SN, and D-962 (all of which are trade names), manufactured by Sakai Chemical Industry Co. The titanium oxide particles may be used singly or in a combination of two or more kinds thereof.

The titanium oxide particles used in the present invention can lower the viscosity of the composition before vulcanizing and can increase the acoustic sensitivity, and therefore titanium oxide particles whose surface has been treated are preferable, and titanium oxide particles subjected to surface treatment with a silicon compound is more preferable. In addition, as described later, with the titanium oxide particles whose surface has been treated, the chemical resistance of the silicone resin for an acoustic wave probe obtained by vulcanizing the composition for an acoustic wave probe of the embodiment of the present invention can be improved. A usual technique may be used as a technique of the surface treatment.

The titanium oxide particles used in the present invention can be subjected to the surface treatment with inorganic compounds and/or organic compounds by usual methods.

For example, inorganic surface treatment with aluminum hydroxide, aluminum oxide, zirconium oxide, silica and/or cerium oxide, and the like can be carried out.

In addition, specific examples of an organic surface-treating agent that can be used for surface treatment include silicone oils such as dimethyl polysiloxane, methyl hydrogen polysiloxane, (dimethicone/methicone) copolymer, methyl phenyl silicone, amino modified silicone, triethoxysilylethyl polydimethylsiloxyethyl dimethicone, and triethoxysilylethyl polydimethylsiloxyethylhexyl dimethicone; alkylsilanes such as capryllysilane, decylsilane, and perfluorooctylsilane; amino acids such as alkyl titanate, alkyl aluminate, polyolefin, polyester, and lauroyl lysine; polyamide and salts thereof; metal soaps such as aluminum stearate, aluminum isostearate, and zinc stearate; and water repellent resin such as nylon, polyester, and polyacrylic. In addition, a coupling agent such as a silane coupling agent or a titanium coupling agent can be used. The surface treatment can be carried out with at least one compound selected from these organic compounds.

In addition, it is also possible to combine inorganic surface treatment and organic surface treatment which are additionally performed. In particular, subjecting the particles to the organic surface treatment is significantly effective because dispersibility of the particles in the composition is improved.

The vinyl group contained in the polysiloxane (A) and the Si—H group contained in the polysiloxane (B) stoichiometrically react with each other in a ratio of 1:1.

However, in the present invention, because gaps between the polysiloxanes (A) and (B) are densely filled with the titanium oxide particles, the movement of the molecular chains of the polysiloxanes (A) and (B) is limited.

Accordingly, the equivalent of the Si—H group contained in the polysiloxane (B) to the vinyl group possessed by the polysiloxane (A) is preferably vinyl group:Si—H group=1:1.1 to 1:8 and more preferably 1:1.2 to 1:5 so that all the vinyl groups react with the Si—H groups.

<Silica Particles (D)>

By the polysiloxane mixture used in the present invention containing the silica particles, not only the effect of improving the acoustic impedance, hardness, mechanical strength, and photoreflectance of the silicone resin for an acoustic wave probe, which is obtained by vulcanizing the composition for an acoustic wave probe of the embodiment of the present invention can be obtained but also the effect of improving the chemical resistance can be obtained. Although the reason why the chemical resistance is improved is not certain, the chemical resistance is considered to be improved due to an effect by the surface treatment applied to the titanium oxide particles and/or silica particles. It is considered that relatively hydrophilic titanium oxide particles and silica particles are uniformly dispersed, and at least one of the particles is subjected to the surface treatment, whereby highly hydrophilic aggregated sites are reduced, and thus the chemical resistance is improved, and particularly an ethanol swelling degree is suppressed.

The silica particles used in the present invention are not particularly limited, but surface-treated silica particles are preferable, and silica particles surface-treated with a silicon compound are more preferable, because it is considered that the viscosity of the composition before vulcanizing is lowered, or the aggregated site of the silica particles is reduced by the surface treatment of the silica particles, thereby becoming excellent in the chemical resistance, and furthermore, the aggregated site where the acoustic wave is likely to scatter is suppressed, and as a result, the acoustic sensitivity becomes higher.

The silica particles used in the present invention can be prepared by a method described later. In addition, it is particularly preferable that the silica particles used in the present invention are in a form in which the surface is treated with a silane compound. It is perceived that the surface treatment of the silica particles with the silane compound strengthens the interaction with the polysiloxane (A) component in the silicone resin and also increases the affinity with the polysiloxane (A) component in the silicone resin, and therefore fine dispersion of the silica particles becomes possible. For this reason, the silica particles surface-treated with the silane compound are more likely to exert a function as a stopper of microcracks generated in a case where a mechanical stress is applied, and can uniformly exert the role thereof by uniformly and finely dispersing in the silicone resin, and therefore the hardness and mechanical strength of the silicone resin are considered to be improved. In addition, the silica particles are finely dispersed in the resin by being subjected to the surface treatment with the silane compound, and the aggregated sites of the hydrophilic silica particles are reduced or eliminated, and thus the entire silicone resin becomes hydrophobic. Therefore, it is considered that the chemical resistance is improved, and particularly the degree of ethanol swelling is suppressed.

A usual technique may be used as a technique of the surface treatment. Examples of the technique of the surface treatment using a silane compound include a technique of performing chemical surface treatment using a silane coupling agent, and a technique of performing coating using a silicone compound.

(i) Silane Coupling Agent

A silane coupling agent having a hydrolyzable group is preferable as a silane coupling agent from the viewpoint of improving the hardness and/or the mechanical strength of a silicone resin. Surface modification of silica particles is performed such that a hydrolyzable group in a silane coupling agent becomes a hydroxyl group after being hydrolyzed using water and this hydroxyl group is subjected to a dehydration and condensation reaction with a hydroxyl group on the surfaces of the silica particles, thereby improving the hardness and/or the mechanical strength of an obtained silicone resin. Examples of the hydrolyzable group include an alkoxy group, an acyloxy group, and a halogen atom.

In a case where the surfaces of silica particles are hydrophobically modified, affinity between the silica particles and the polyorganosiloxane (A) becomes favorable, and therefore, the hardness and the mechanical strength of an obtained silicone resin are improved, which is preferable. In addition, the entire silicone resin becomes hydrophobic, and therefore the chemical resistance is improved, and the degree of ethanol swelling is suppressed.

Examples of a silane coupling agent having a hydrophobic group as a functional group include alkoxysilanes such as methyltrimethoxysilane (MTMS), dimethyldimethoxysilane, phenyltrimethoxysilane, methyltriethoxysilane, dimethyldiethoxysilane, phenyltriethoxysilane, n-propyltrimethoxysilane, n-propyltriethoxysilane, hexyltrimethoxysilane, hexyl triethoxysilane, and decyltrimethoxysilane; chlorosilanes such as methyltrichlorosilane, dimethyldichlorosilane, trimethylchlorosilane, and phenyltrichlorosilane; and hexamethyldisilazane (HMDS).

In addition, examples of a silane coupling agent having a vinyl group as a functional group include alkoxysilanes such as methacryloxypropyltriethoxysilane, methacryloxypropyltrimethoxysilane, methacryloxypropylmethyldiethoxysilane, methacryloxypropylmethyldimethoxysilane, vinyltriethoxysilane, vinyltrimethoxysilane, and vinylmethyldimethoxysilane; chlorosilanes such as vinyltrichlorosilane and vinylmethyldichlorosilane; and divinyltetramethyldisilazane.

Silica particles surface-treated with a silane coupling agent are preferably silica particles treated with a trialkylsilylating agent, and more preferably silica particles treated with a trimethylsilylating agent, because the aggregation force between the particles decreases, and thus the viscosity of the polysiloxane mixture becomes low, and the aggregated sites that are easily light-scattered due to the fine and uniform dispersion of the particles decrease or disappear, and thus an acoustic damping coefficient becomes lower.

Examples of the silane compound include the above-described silane coupling agents and a silane coupling agent in which a functional group in a silane coupling agent is substituted by an alkyl group.

In addition, examples of the trimethylsilylating agent include trimethylchlorosilane and hexamethyldisilazane (HMDS) described in the above-described silane coupling agent, and methyltrimethoxysilane (MTMS) and trimethylmethoxysilane which are silane coupling agents in which a functional group is substituted by an alkyl group.

Examples of a commercially available silane coupling agent include hexamethyldisilazane (HMDS) (trade name: HEXAMETHYLDISILAZANE (SIH6110.1) manufactured by GELEST, INC.).

A hydroxyl group existing on the surfaces of silica particles is covered with a trimethylsilyl group through a reaction with hexamethyldisilazane (HMDS), methyltrimethoxysilane (MTMS), trimethylmethoxysilane, and the like and the surfaces of the silica particles are hydrophobically modified.

In the present invention, the silane coupling agent may be used alone or in a combination of two or more thereof.

(ii) Silicone Compound

A silicone compound with which the silica particles are coated may be a polymer formed through siloxane bonding. Examples of the silicone compound include a silicone compound in which all or a part of side chains and/or terminals of polysiloxane has become a methyl group, a silicone compound in which a part of a side chain is a hydrogen atom, a modified silicone compound in which organic groups such as an amino group and/or an epoxy group is introduced into all or a part of side chains and/or terminals, and a silicone resin having a branched structure. The silicone compound may be either of a linear structure or a cyclic structure.

Examples of the silicone compound in which all or a part of side chains and/or terminals of polysiloxane has become a methyl group include monomethylpolysiloxane such as polymethylhydrosiloxane (hydride terminated), polymethylhydrosiloxane (trimethylsiloxy terminated), polymethylphenylsiloxane (hydride terminated), and polymethylphenylsiloxane (trimethylsiloxy terminated); and dimethylpolysiloxanes such as dimethylpolysiloxane (hydride terminated), dimethylpolysiloxane (trimethylsiloxy terminated), and cyclic dimethylpolysiloxane.

Examples of the silicone compound in which a part of side chains is a hydrogen atom include methylhydrosiloxane-dimethylsiloxane copolymer (trimethylsiloxy terminated), methylhydrosiloxane-dimethylsiloxane copolymer (hydride terminated), polymethylhydrosiloxane (hydride terminated), polymethylhydrosiloxane (trimethylsiloxy terminated), polyethylhydrosiloxane (triethylsiloxy terminated), polyphenyl-(dimethylhydrosiloxy) siloxane (hydride terminated), methylhydrosiloxane-phenylmethylsiloxane copolymer (hydride terminated), methylhydrosiloxane-octylmethylsiloxane copolymer, and methylhydrosiloxane-octylmethylsiloxane-dimethylsiloxane terpolymer.

In addition, examples of modified silicone into which an organic group is introduced include reactive silicone into which an amino group, an epoxy group, a methoxy group, a (meth)acryloyl group, a phenoxy group, a carboxylic anhydride group (—C(=O)—O—C(=O)—R (R representing a substituent such as an alkyl group), a hydroxy group, a sulfanyl group, a carboxyl group, and/or an organic group of a hydrogen atom are introduced; and non-reactive silicone modified with polyether, aralkyl, fluoroalkyl, long chain alkyl, long chain aralkyl, higher fatty acid ester, higher fatty acid amide, and/or polyether methoxy.

Silica particles coated with a silicone compound can be obtained through a usual method. For example, the silica particles can be obtained by being mixed and stirred in dimethylpolysiloxane at 50° C. to 150° C. for a certain period of time and being filtered.

In addition, in a case of using reactive modified silicone as a silicone compound, surface modification of silica particles is performed through reaction of an organic group with a hydroxyl group of the surfaces of the silica particles, and therefore, the hardness and/or the mechanical strength of an obtained silicone resin is improved. In addition, the dispersibility of the silica particles is improved by the surface treatment, and the aggregated sites of the hydrophilic silica particles are reduced or eliminated, and thus the entire silicone resin becomes hydrophobic. Therefore, it is considered that the chemical resistance is improved, and the degree of ethanol swelling is suppressed.

An Example of the commercially available silicone compound includes methyl hydrogen silicone oil (MHS) (trade name: KF-99, manufactured by Shin-Etsu Chemical Co., Ltd.) which is polymethylhydrosiloxane (trimethylsiloxy terminated).

The average primary particle diameter of the silica particles used in the present invention is preferably 1 nm to 200 nm, more preferably 3 nm to 100 nm, and even more preferably 5 nm to 40 nm from the viewpoints of suppressing increase in the viscosity of the composition for an acoustic wave probe before vulcanizing, suppressing increase in the acoustic attenuation of the silicone resin, and improving the tear strength. With the conditions in which the average primary particle diameter of the titanium oxide particles is within the above-described range, the average primary particle diameter of the silica particles is within the above-described range, and the average primary particle diameter of the titanium oxide particles is larger than the average primary particle diameter of the silica particles, the silica particles exist between the titanium oxide particle and the titanium oxide particle, and thus the cohesive force between the titanium oxide particles and the silica particles increases to form a pseudo-crosslinked structure, and therefore the chemical resistance is further improved. In particular, it is considered that the above description is due to good surface potential compatibility between the titanium oxide particles and the silica particles, but the light reflectance also becomes high, and the hardness and the tear strength also become high in order to form the homogeneous pseudo-crosslinked structure.

Here, the average primary particle diameter means a volume average particle diameter. The volume average particle diameter can be obtained by, for example, measuring the particle diameter distribution using a laser diffraction scattering type particle diameter distribution measurement apparatus (for example, trade name "LA910" manufactured by HORIBA, Ltd.). In the present specification, for silica particles of which the average primary particle diameter has not been disclosed in the catalog or for silica particles newly manufactured, the average primary particle diameter is obtained through the above-described measurement method.

Here, the average primary particle diameter of the silica particles means an average primary particle diameter in a state in which the surface treatment has been performed.

The silica particles may be used singly or in a combination of two or more thereof.

The specific surface area of the silica particles used in the present invention is preferably 1 to 400 $m^2/g$, more preferably 5 to 200 $m^2/g$, and particularly preferably 10 to 100 $m^2/g$ from the viewpoint of improving the hardness and/or the mechanical strength and improving the chemical resistance of a silicone resin to be obtained.

The degree of surface modification of the silica particles, that is, the degree of hydrophobicity of the silica particles can be examined by the following degree of methanol hydrophobicity.

The degree of methanol hydrophobicity of the silica particles which is calculated through the following methanol titration test is preferably 40 to 80 mass %, more preferably 50 to 80 mass %, and still more preferably 60 to 80 mass %. Here, the larger the degree of methanol hydrophobicity, the higher the hydrophobicity, and the smaller the degree of methanol hydrophobicity, the higher the hydrophilicity.

The degree of methanol hydrophobicity can be obtained by a calculation method to be described later in a section of examples.

In a case where the degree of methanol hydrophobicity is within the above-described preferred ranges, it is possible to suppress decrease in acoustic sensitivity in a case where a silicone resin for an acoustic wave probe is obtained, and furthermore, it is possible to suppress the degree of ethanol swelling, without increase in the viscosity of the composition for an acoustic wave probe before vulcanizing.

The silica particles are preferably spherical.

The Wardell's sphericity of a primary particle of the silica particles is preferably 0.7 to 1, more preferably 0.8 to 1, and still more preferably 0.9 to 1.

Here, the "Wardell's sphericity" (refer to Chemical Engineering Handbook published by Maruzen Inc.) is an index obtained by measuring the sphericity of a particle as (diameter of circle equal to projection area of particle)/(diameter of minimum circle circumscribing projection image of particle). A particle having the index closer to 1.0 means a particle closer to a true sphere.

It is possible to use, for example, a scanning electron microscope (SEM) photograph can be used to measure the Wardell's sphericity (hereinafter, also simply referred to as sphericity). Specifically, for example, about 100 primary particles are randomly observed using the SEM photograph, and each sphericity thereof is calculated. An average value obtained by dividing the total of the calculated sphericities by the number of observed primary particles is regarded as the sphericity.

In a case where the Wardell's sphericity is within the above-described preferred ranges, it is considered that the acoustic sensitivity is improved because the area of the acoustic wave hitting the silica particles becomes smaller in a case where the silicone resin is irradiated with the acoustic wave. In particular, it is considered that the anisotropy against ultrasonic scattering decreases and thus the acoustic sensitivity is more effectively improved in a case where the shapes of the silica particles are truly spherical within a specific range of the average primary particle diameter of the silica particle used in the present invention. In addition, since the hydrophilic part is locally reduced, the chemical resistance is improved.

In this specification, the "true spherical shape" also includes a slightly distorted sphere of which the Wardell's sphericity is within a range of 0.9 to 1.

The silica particles are roughly classified into combustion method silica (that is, fumed silica) obtained by burning a silane compound, deflagration method silica obtained by explosively burning metallic silicon powder, wet-type silica (among which silica synthesized under alkaline conditions is referred to as precipitation method silica and silica synthesized under acidic conditions is referred to as gel method silica) obtained through a neutralization reaction with sodium silicate and mineral acid, and sol-gel method silica (so-called Stoeber method) obtained through hydrolysis of hydrocarbyloxysilane depending on its production method.

Preferred examples of a method for producing truly spherical silica particles include an explosion method and a sol-gel method.

The sol-gel method is a method of obtaining hydrophilic spherical silica particles essentially consisting of $SiO_2$ units by hydrolyzing and condensing a hydrocarbyloxysilane (preferably tetrahydrocarbyloxysilane) or a partial hydrolytic condensation product thereof or a combination thereof.

In addition, the hydrophobic treatment of the surfaces of the silica particles can also be carried out by introducing $R^3_3SiO_{1/2}$ units ($R^3$'s are the same as or different from each other and are substituted or unsubstituted monovalent hydrocarbon groups having 1 to 20 carbon atoms) onto the surfaces of hydrophilic spherical silica particles.

Specifically, the hydrophobic treatment thereof can be carried out, for example, through methods disclosed in JP2007-099582A and JP2014-114175A.

<Other Components>

In the composition for an acoustic wave probe of the embodiment of the present invention, it is possible to appropriately formulate a platinum catalyst for an addition polymerization reaction, a vulcanization retardant, a solvent, a dispersant, a pigment, a dye, an antistatic agent, an antioxidant, a flame retardant, a thermal conductivity enhancer, and the like in addition to the polysiloxane (A) having a vinyl group and a phenyl group, the polysiloxane having two or more Si—Hl groups in a molecular chain, the titanium oxide particles, and the silica particles.

<Catalyst>

Examples of the catalyst include platinum or a platinum-containing compound (hereinafter referred to as "platinum compound"). Any platinum or platinum compound can be used.

Specific examples thereof include a catalyst in which platinum black or platinum is carried on an inorganic compound, carbon black, or the like; platinum chloride or an alcohol solution of platinum chloride; a complex salt of platinum chloride and olefin; and a complex salt of platinum chloride and vinyl siloxane. The catalyst may be used singly, or in a combination of two or more thereof.

A content of the catalyst can be appropriately set within the range of the catalyst amount.

The catalyst is necessary in the hydrosilylation reaction in which the Si—H group of the polysiloxane (B) is added to the vinyl group of the polysiloxane (A). The polysiloxane (A) is cross-linked by the polysiloxane (B) due to an additional vulcanization reaction by hydrosilylation, and therefore a silicone resin is formed.

Here, the catalyst may be contained in the composition for an acoustic wave probe of the embodiment of the present invention or may be brought into contact with the composition for an acoustic wave probe without being contained in the composition for an acoustic wave probe. The latter case is preferable.

Examples of commercially available platinum catalyst include platinum compounds (a trade name of PLATINUM CYCLOVINYLMETHYLSILOXANE COMPLEX IN CYCLIC METHYLVINYLSILOXANES (SIP6832.2).

In a case where the catalyst is present in the polysiloxane mixture, from the viewpoint of reactivity, the amount of the catalyst present is preferably 0.00001 parts by mass or more, more preferably 0.0002 parts by mass or more, even more preferably 0.0005 parts by mass or more, and particularly preferably 0.0001 parts by mass or more, as a Pt amount with respect to 100 parts by mass of the polysiloxane mixture. Meanwhile, the amount is preferably 0.1 parts by mass or less, more preferably 0.05 parts by mass or less, even more preferably 0.01 parts by mass or less, and particularly preferably 0.005 parts by mass or less.

In addition, it is possible to control the vulcanization temperature by selecting an appropriate platinum catalyst. For example, platinum-vinyldisiloxane is used for room temperature vulcanization (RTV) at lower than or equal to 50° C. and platinum-cyclic vinylsiloxane is used for high temperature vulcanization (HTV) at higher than or equal to 130° C.

<Method for Producing Composition for Acoustic Wave Probe and Silicone Resin for Acoustic Wave Probe>

The composition for an acoustic wave probe of the embodiment of the present invention can be prepared by a usual method.

For example, the composition for an acoustic wave probe can be obtained by kneading components constituting the composition for an acoustic wave probe using a kneader, a pressure kneader, a Banbury mixer (continuous kneader), and a kneading device with two rolls. The order of mixing the components is not particularly limited.

It is preferable to first make a polysiloxane mixture in which the titanium oxide particles and silica particles are dispersed in the polysiloxane (A) having a vinyl group and a phenyl group and the polysiloxane (B) having two or more Si—H groups in a molecular chain, from the viewpoint of obtaining a homogeneous composition. Thereafter, it is possible to prepare a composition for an acoustic wave probe after adding a catalyst to the polysiloxane mixture, in which the titanium oxide particles and silica particles are dispersed, and performing defoamation under reduced pressure.

It is possible to obtain a silicone resin for an acoustic wave probe of the embodiment of the present invention by vulcanizing the composition for an acoustic wave probe of the embodiment of the present invention which has been obtained in this manner. Specifically, it is possible to obtain a silicone resin for an acoustic wave probe by, for example, thermally vulcanizing the composition for an acoustic wave probe for 5 minutes to 500 minutes at 20° C. to 200° C.

<Characteristics of Silicone Resin>

Hereinafter, the characteristics of the silicone resin will be described in detail.

Here, ultrasonic characteristics among the acoustic characteristics will be described. However, the acoustic characteristics are not limited to the ultrasonic characteristics, and relates to acoustic characteristics at an appropriate frequency which is selected in accordance with a test object, measurement conditions, or the like.

[Hardness]

The hardness is preferably 30 or more and more preferably 35 or more. A practical upper limit value is 80 or less. With the hardness within the above-described range, it is possible to prevent deformation in a case where the silicone resin is incorporated as a part of the acoustic wave probe and used.

The hardness of a silicone resin sheet can be obtained by a measurement method to be described later in a section of examples.

[Tear Strength]

The tear strength is preferably greater than or equal to 6 N/cm and more preferably greater than or equal to 10 N/cm. A practical upper limit value is less than or equal to 100 N/cm.

The tear strength can be obtained by a measurement method to be described later in a section of examples.

[Degree of Ethanol Swelling (Chemical Resistance)]

The degree of ethanol swelling is preferably 10% or less and more preferably 8% or less. A practical lower limit value is 4% or more.

The degree of ethanol swelling can be obtained by a measurement method to be described later in a section of examples.

[Total Light Reflectance (Photoreflectance)]

The total light reflectance is preferably 95% or more and more preferably 96% or more. A practical upper limit value is 99% or less.

The total light reflectance can be obtained by a measurement method to be described later in a section of examples.

[Acoustic Impedance]

The acoustic impedance of the silicone resin sheet is preferably as close to that of the living body ($1.40 \times 10^6$ to $1.70 \times 10^6$ kg/m$^2$/sec). The acoustic impedance of the silicone resin sheet of the present invention is preferably $1.25 \times 10^6$ to $1.80 \times 10^6$ kg/m$^2$/sec, more preferably $1.30 \times 10^6$ to $1.70 \times 10^6$ kg/m$^2$/sec, and particularly preferably $1.40 \times 10^6$ to $1.60 \times 10^6$ kg/m$^2$/sec.

The acoustic impedance can be obtained by a method to be described later in a section of examples.

[Acoustic (Ultrasonic) Sensitivity]

In an evaluation system in the present invention, the acoustic (ultrasonic) sensitivity is preferably greater than or equal to −74 dB, and more preferably greater than or equal to −73 dB. A practical upper limit value is less than or equal to −60 dB.

The acoustic (ultrasonic) sensitivity can be obtained by a method to be described later in a section of examples.

The composition for an acoustic wave probe of the embodiment of the present invention is useful for medical members and can preferably be used, for example, in an acoustic wave probe and an acoustic wave measurement apparatus. The acoustic wave measurement apparatus of the embodiment of the present invention is not limited to an ultrasound diagnostic apparatus and a photoacoustic wave measurement apparatus, and is referred to as an apparatus that receives an acoustic wave which has been reflected or generated from a test object and displays the received acoustic wave as an image or a signal strength.

Particularly, the composition for an acoustic wave probe of the embodiment of the present invention can suitably be used in: a material of an acoustic matching layer which is provided in an acoustic lens of an ultrasound diagnostic apparatus or between a piezoelectric element and the acoustic lens and plays a role of matching acoustic impedance between the piezoelectric element and the acoustic lens; a material of an acoustic lens in a photoacoustic wave measurement apparatus or an ultrasound endoscope: and a material or the like of an acoustic lens in an ultrasound probe comprising capacitive micromachined ultrasonic transducers (cMUT) as an ultrasonic transducer array.

Specifically, the silicone resin for an acoustic wave probe of the embodiment of the present invention is preferably applied to, for example, an ultrasound diagnostic apparatus disclosed in JP2005-253751A and JP2(003-169802A or an acoustic wave measurement apparatus such as a photoacoustic wave measurement apparatus disclosed in JP2013-202050A, JP2013-188465A. JP2013-180330A. JP2013-158435A, JP2013-154139A, and the like.

<Acoustic Wave Probe>

Hereinafter, a configuration of an acoustic wave probe of the embodiment of the present invention will be described in more detail based on a configuration of an ultrasound probe in an ultrasound diagnostic apparatus which is described in FIG. 1. The ultrasound probe is a probe which particularly uses an ultrasonic wave as an acoustic wave in an acoustic wave probe. For this reason, a basic configuration of the ultrasound probe can be applied to the acoustic wave probe.

<Ultrasound Probe>

An ultrasound probe 10 is a main component of the ultrasound diagnostic apparatus and has a function of generating an ultrasonic wave and transmitting and receiving an ultrasonic beam. The configuration of the ultrasound probe 10 is provided in the order of an acoustic lens 1, an acoustic matching layer 2, a piezoelectric element layer 3, and a backing material 4 from a distal end (the surface coming into contact with a living body which is a test object) as shown in FIG. 1. In recent years, an ultrasound probe having a laminated structure in which an ultrasonic transducer (piezoelectric element) for transmission and an ultrasonic transducer (piezoelectric element) for reception are formed of materials different from each other has been proposed in order to receive high-order harmonics.

<Piezoelectric Element Layer>

The piezoelectric element layer 3 is a portion which generates an ultrasonic wave and in which an electrode is attached to both sides of a piezoelectric element. In a case where voltage is applied to the electrode, the piezoelectric element layer generates an ultrasonic wave through repeated contraction and expansion of the piezoelectric element and through vibration.

Inorganic piezoelectric bodies of so-called ceramics obtained by polarizing crystals, single crystals such as $LiNbO_3$, $LiTaO_3$, and $KNbO_3$, thin films of ZnO and AlN, $Pb(Zr, Ti)O_3$-based sintered body, and the like are widely used as the material constituting a piezoelectric element. In general, piezoelectric ceramics such as lead zirconate titanate (PZT) with good conversion efficiency are used.

In addition, sensitivity having a wider band width is required for a piezoelectric element detecting a reception wave on a high frequency side. For this reason, an organic piezoelectric body has been used in which an organic polymer material such as polyvinylidene fluoride (PVDF) is used as the piezoelectric element being suitable for a high frequency or a wide band.

Furthermore, cMUT using micro electro mechanical systems (MEMS) technology in which an array structure, which shows excellent short pulse characteristics, excellent broadband characteristics, and excellent mass productivity and has less characteristic variations, is obtained is disclosed in JP2011-071842A or the like.

In the present invention, it is possible to preferably use any piezoelectric element material.

<Backing Material>

The backing material 4 is provided on a rear surface of the piezoelectric element layer 3 and contributes to the improvement in distance resolution in an ultrasonic diagnostic image by shortening the pulse width of an ultrasonic wave through the suppression of excess vibration.

<Acoustic Matching Layer>

The acoustic matching layer 2 is provided in order to reduce the difference in acoustic impedance between the piezoelectric element layer 3 and a test object and to efficiently transmit and receive an ultrasonic wave.

A composition for an ultrasound probe of the embodiment of the present invention can preferably be used as a material for the acoustic matching layer since the difference in acoustic impedance ($1.40 \times 10^6$ to $1.70 \times 10^6$ $kg/m^2/sec$) between the piezoelectric element layer and a human body is small. The acoustic matching layer used in the acoustic wave probe of the embodiment of the present invention preferably contains 10 mass % or more of a silicone resin for an acoustic wave probe obtained by subjecting the composition for an acoustic wave probe of the embodiment of the present invention to a vulcanization reaction.

<Acoustic Lens>

The acoustic lens 1 is provided in order to improve resolution by making an ultrasonic wave converge in a slice direction using refraction. In addition, it is necessary for the acoustic lens to achieve matching of an ultrasonic wave with acoustic impedance ($1.40 \times 10^6$ to $1.70 \times 10^6$ $kg/m^2/sec$ in a case of a human body) of a living body which is a test object after being closely attached to the living body and to reduce ultrasonic attenuation of the acoustic lens 1 itself.

That is, sensitivity of transmission and reception of an ultrasonic wave is improved in a case where the acoustic velocity is sufficiently lower than that of a human body, the ultrasound attenuation is low, or the acoustic impedance is close to a value of the skin of a living body such as a human body, as the material of the acoustic lens 1.

The composition for an ultrasound probe of the embodiment of the present invention can also preferably be used as a material of the acoustic lens. The acoustic lens of the embodiment of the present invention preferably contains 10 mass % or more of a silicone resin for an acoustic wave probe obtained by subjecting the composition for an acoustic wave probe of the present invention to a vulcanization reaction.

The operation of the ultrasound probe 10 having such a configuration will be described. The piezoelectric element layer 3 is resonated after applying voltage to the electrodes provided on both sides of a piezoelectric element, and an ultrasound signal is transmitted to a test object from the acoustic lens. During reception of the ultrasonic signal, the piezoelectric element layer 3 is vibrated using the signal (echo signal) reflected from the test object and this vibration is electrically converted into a signal to obtain an image.

Particularly, a remarkable effect of improving the sensitivity can be checked from a transmission frequency of an ultrasonic wave of greater than or equal to about 5 MHz using the acoustic lens obtained from the composition for an ultrasound probe of the embodiment of the present invention as a general medical ultrasonic transducer. Particularly, a remarkable effect of improving the sensitivity can particularly be expected from a transmission frequency of an ultrasonic wave of greater than or equal to 10 MHz.

Hereinafter, an apparatus in which the acoustic lens obtained from the composition for an ultrasound probe of the embodiment of the present invention exhibits a function particularly regarding conventional problems will be described in detail.

The composition for an ultrasound probe of the embodiment of the present invention exhibits an excellent effect even with respect to other apparatuses disclosed below.

<Ultrasound Probe Comprising Capacitive Micromachined Ultrasonic Transducer (cMUT)>

In a case where cMUT apparatuses disclosed in JP2006-157320A, JP2011-071842A, and the like are used in an ultrasonic transducer array, the sensitivity thereof generally becomes low compared to a transducer in which usual piezoelectric ceramics (PZT) is used.

However, it is possible to make up for deficient sensitivity of cMUT using the acoustic lens obtained from the composition for an acoustic wave probe of the embodiment of the present invention. Accordingly, it is possible to make the sensitivity of cMUT to performance of a conventional transducer.

The cMUT apparatus is manufactured through MEMS technology. Therefore, it is possible to provide an inexpensive ultrasound probe, of which mass productivity is higher than that of a piezoelectric ceramics probe, to the market.

<Photoacoustic Wave Measurement Apparatus Using Photo-Ultrasound Imaging>

Photo-ultrasound imaging (photoacoustic imaging: PAI) disclosed in JP2013-158435A or the like displays a signal strength of an ultrasonic wave or an image obtained by imaging the ultrasonic wave generated in a case where human tissue is adiabatically expanded using light (magnetic wave) with which the interior of a human body is irradiated.

Here, the amount of an acoustic pressure of an ultrasonic wave generated through light irradiation is minute, and therefore, there is a problem in that it is difficult to observe deeper regions of a human body.

However, it is possible to exhibit an effect effective for the problem using the acoustic lens obtained from the composition for an acoustic wave probe of the embodiment of the present invention.

<Ultrasound Endoscope>

In an ultrasonic wave in an ultrasound endoscope disclosed in JP2008-311700A or the like, a signal line cable is structurally long compared to that of a transducer for a body surface, and therefore, there is a problem of improving the sensitivity of the transducer due to loss of the cable. Regarding this problem, it is said that there are no effective means for improving the sensitivity due to the following reasons.

First in a case of an ultrasound diagnostic apparatus for a body surface, it is possible to install an amplifier circuit, an AD conversion IC, or the like at a distal end of the transducer. In contrast, the ultrasound endoscope is inserted into a body. Therefore, there is no installation space within the transducer, and thus, installation at a distal end of transducers is difficult.

Secondly, it is difficult to apply a piezoelectric single crystal employed in the transducer in the ultrasound diagnostic apparatus for a body surface onto a transducer with an ultrasonic transmission frequency of greater than or equal to 7 to 8 MHz due to physical properties and processing suitability. However, an ultrasonic wave for an endoscope is generally a probe having an ultrasonic transmission frequency of greater than or equal to 7 to 8 MHz, and therefore, it is also difficult to improve the sensitivity by the piezoelectric single crystal material.

However, it is possible to improve the sensitivity of the ultrasonic transducer for an endoscope using the acoustic lens obtained from the composition for an acoustic wave probe of the embodiment of the present invention.

In addition, even in a case of using the same ultrasonic transmission frequency (for example, 10 MHz), the efficacy is particularly exhibited in a case of using the acoustic lens obtained from the composition for an acoustic wave probe of the embodiment of the present invention in the ultrasonic transducer for an endoscope.

EXAMPLES

The present invention will be described in more detail based on Examples in which an ultrasonic wave is used as an acoustic wave. The present invention is not limited to the ultrasonic wave, and any acoustic wave of an audible frequency may be used as long as an appropriate frequency is selected in accordance with a test object, measurement conditions, and the like.

Example 1

57.4 parts by mass of a vinyl terminated diphenylsiloxane-dimethylsiloxane copolymer (component (A) in Table 1, "PDV-0541" (trade name) manufactured by GELEST, INC. with a mass average molecular weight of 60,000 and a diphenylsiloxane amount of 5 mol %); 0.6 parts by mass of methylhydrosiloxane polymer (component (B) in Table 1, "HMS-991" (trade name) manufactured by GELEST, INC. with a mass average molecular weight of 1,600 and an Si—H equivalent of 67 g/mol); 24.0 parts by mass of titanium oxide particles (component (C) in Table 1, "TITONE (registered trademark) R-24" manufactured by Sakai Chemical Industry Co. with an average primary particle diameter of 200 nm, silica-alumina-organic surface treatment); and 18.0 parts by mass of fumed silica (component (D) in Table 1, "AEROSIL (registered trademark) RX300," average primary particle diameter of 7 nm, hexamethyldisilazane (HMDS)-surface-treated product) were kneaded with a kneader at a temperature of 23° C. for 2 hours, and therefore a homogeneous paste was obtained. 500 ppm (10 ppm as platinum) of a platinum catalyst solution (SIP6832.2, manufactured by GELEST, INC., 2% platinum concentration) was added to and mixed with the paste. Then, the mixture was subjected to defoamation under reduced pressure, placed in a metal mold of 150 mm×150 mm, and subjected to heat treatment for 3 hours at 60° C., and therefore a silicone resin sheet having a thickness of 0.4 mm was obtained.

In the same manner as described above, a silicone resin sheet having a thickness of 2 mm was obtained.

Examples 2 to 20 and Comparative Examples 1 to 3

Predetermined silicone resin sheets were produced in the same manner as Example 1 except that the composition was changed to the compositions described in Table 1.

[Degree of Methanol Hydrophobicity]

50 ml of ion exchange water and 0.2 g of silica particles as samples were placed in a beaker at 25° C. and stirred with a magnetic stirrer, methanol was added dropwise thereto from a burette, and the amount (Xg) of methanol added dropwise until the whole sample settles was measured. The degree of methanol hydrophobicity was calculated using the following equation.

Degree of methanol hydrophobicity (mass %)=$X/(50+X) \times 100$

<Evaluation of Each Characteristic>

The following evaluation was performed on silicone resin sheets of Examples 1 to 20 and Comparative Examples 1 to 3.

[Hardness]

The type A durometer hardness of each of the obtained silicone resin sheets with a thickness of 2 mm was measured using a rubber hardness meter ("RH-201A" (trade name) manufactured by Excel co., Ltd.) in compliance with JIS K6253-3 (2012). The hardness is described as JIS hardness in Table 1.

[Tear Strength]

A trouser-type test piece of a silicone resin sheet with a thickness of 2 mm was manufactured and the tear strength was measured in compliance with JIS K6252 (2007).

[Degree of Ethanol Swelling]

A mass (A) of the obtained silicone resin sheet having a thickness of 2 mm was measured and a mass (B) after immersion in ethanol at 23° C. for 48 hours was measured respectively, and the degree of swelling (S [% by mass]) was obtained by the following formula.

Degree of swelling [$S$]=$(B-A)/A \times 100$

[Total Light Reflectance]

The reflectance of the obtained sheet having a thickness of 0.4 mm at a wavelength of 755 nm was measured using a spectrophotometer (integrating sphere unit) of U-3310 type manufactured by Hitachi, Ltd. according to JIS K 7375 (2008).

[Acoustic Impedance]

The density of each of the obtained silicone resin sheets with a thickness of 2 mm at 25° C. was measured using an electronic gravimeter (a trade name of "SD-200L" manufactured by ALFA MIRAGE) in accordance with a density measurement method of a method A (underwater substitution method) disclosed in JIS K7112 (1999). The acoustic velocity of an ultrasonic wave was measured at 25° C. using a sing-around type acoustic velocity measurement apparatus (a trade name of "UVM-2 type" manufactured by Ultrasonic Engineering Co., Ltd.) in compliance with JIS Z2353 (2003) and acoustic impedance was obtained from a sum of the density and the acoustic velocity which had been measured.

[Acoustic (Ultrasonic) Attenuation and Acoustic (Ultrasonic) Sensitivity]

A sinusoidal signal (a wave) of 5 MHz which had been output from an ultrasound oscillator (a function generator with a trade name of "FG-350" manufactured by IWATSU ELECTRIC CO., LTD.) was input into an ultrasound probe (manufactured by JAPAN PROBE), and an ultrasound pulse wave with a center frequency of 5 MHz was generated in water from the ultrasound probe. The magnitude of the amplitude before and after the generated ultrasonic wave passed through each of the obtained silicone resin sheets with a thickness of 2 mm was measured in a water temperature environment of 25° C. using an ultrasound receiver (an oscilloscope with a trade name of "VP-5204A" manufactured by Matsushita Electric Industrial Co., Ltd.) The acoustic (ultrasonic) attenuation of each material was compared with each other by comparing the acoustic (ultrasonic) sensitivities of each material.

The acoustic (ultrasonic) sensitivity is a numerical value given by the following calculation equation.

In the following calculation equation, Vin represents a voltage peak value of an input wave which is generated by the ultrasound oscillator and has a half-width of less than or equal to 50 nsec. Vs represents a voltage value obtained when the ultrasound oscillator receives an acoustic wave (ultrasonic wave) that the acoustic wave (ultrasonic wave) generated passes through a sheet and is reflected from an opposite side of the sheet. As the acoustic (ultrasonic) sensitivity becomes high, the acoustic (ultrasonic) attenuation becomes low.

Acoustic (Ultrasonic) sensitivity=$20 \times \mathrm{Log}(Vs/Vin)$

The obtained results were summarized and shown in Table 1.

In Table 1, the mass average molecular weight of the polysiloxane (component (A)) and the polysiloxane (component (B)) is simply described as a molecular weight, and the type of each component is indicated by a trade name.

TABLE 1

| | | | Example 1 | Example 2 | Example 3 | Example 4 | Example 5 | Example 6 | Example 7 | Example 8 |
|---|---|---|---|---|---|---|---|---|---|---|
| Mixed composition | Component (A) | Type | PDV-0541 | PDV-0535 | PDV-1641 | PDV-1635 | PDV-1631 | PDV-0541 | PDV-0541 | PDV-0541 |
| | | Molecular weight | 60,000 | 47,500 | 55,000 | 35,300 | 19,000 | 60,000 | 60,000 | 60,000 |
| | | Content [parts by mass] | 57.4 | 57.2 | 56.3 | 56.1 | 53.5 | 57.4 | 57.4 | 57.4 |
| | Component (B) | Type | HMS-991 | HMS-991 | HPM-502 | HPM-502 | HPM-502 | HMS-991 | HMS-991 | HMS-991 |
| | | Molecular weight | 1,600 | 1,600 | 4,500 | 4,500 | 4,500 | 1,600 | 1,600 | 1,600 |
| | | Content [parts by mass] | 0.6 | 0.8 | 1.7 | 1.9 | 4.5 | 0.6 | 0.6 | 0.6 |
| | Component (C) | Type | R-24 | R-24 | R-24 | R-24 | R-24 | R-24 | R-24 | R-24 |
| | | Average primary particle diameter [nm] | 200 | 200 | 200 | 200 | 200 | 200 | 200 | 200 |
| | | Content [parts by mass] | 24.0 | 24.0 | 24.0 | 24.0 | 24.0 | 32.0 | 27.0 | 21.0 |

TABLE 1-continued

|  |  |  |  |  |  |  |  |  |  |  |
|---|---|---|---|---|---|---|---|---|---|---|
|  |  | Component (D) | Type | RX300 | RX300 | RX300 | RX300 | RX300 | RX300 | RX300 | RX300 |
|  |  |  | Average primary particle diameter [nm] | 7 | 7 | 7 | 7 | 7 | 7 | 7 | 7 |
|  |  |  | Degree of MeOH hydrophobicity [%] | 35 | 35 | 35 | 35 | 35 | 35 | 35 | 35 |
|  |  |  | Content [parts by mass] | 18.0 | 18.0 | 18.0 | 18.0 | 18.0 | 10.0 | 15.0 | 21.0 |
| Evaluation |  | JIS hardness |  | 45 | 47 | 43 | 45 | 47 | 41 | 43 | 46 |
|  |  | Tear strength [N/cm] |  | 40 | 32 | 19 | 15 | 10 | 24 | 33 | 44 |
|  |  | Ethanol swelling degree [% by mass] |  | 8 | 8 | 9 | 8 | 7 | 7 | 8 | 8 |
|  |  | Total light reflectance [%] |  | 97 | 97 | 97 | 97 | 97 | 98 | 97 | 96 |
|  |  | Acoustic impedance [×$10^6$ kg/m²/sec] |  | 1.37 | 1.38 | 1.53 | 1.54 | 1.54 | 1.39 | 1.38 | 1.36 |
|  |  | Acoustic (ultrasonic) sensivity [dB] |  | −71.2 | −71.4 | −71.6 | −71.8 | −72.0 | −72.5 | −71.8 | −70.9 |

|  |  |  | Example 9 | Example 10 | Example 11 | Example 12 | Example 13 | Example 14 | Example 15 | Example 16 |
|---|---|---|---|---|---|---|---|---|---|---|
| Mixed composition | Component (A) | Type | PDV-0541 | PDV-0541 | PDV-0541 | PDV-0541 | PDV-0541 | PDV-0541 | PDV-0541 | PDV-0541 |
|  |  | Molecular weight | 60,000 | 60,000 | 60,000 | 60,000 | 60,000 | 60,000 | 60,000 | 60,000 |
|  |  | Content [parts by mass] | 57.4 | 57.4 | 57.4 | 57.4 | 57.4 | 57.4 | 57.4 | 57.4 |
|  | Component (B) | Type | HMS-991 | HMS-991 | HMS-991 | HMS-991 | HMS-991 | HMS-991 | HMS-991 | HMS-991 |
|  |  | Molecular weight | 1,600 | 1,600 | 1,600 | 1,600 | 1,600 | 1,600 | 1,600 | 1,600 |
|  |  | Content [parts by mass] | 0.6 | 0.6 | 0.6 | 0.6 | 0.6 | 0.6 | 0.6 | 0.6 |
|  | Component (C) | Type | R-3 L SN | D-962 | R-45M | R-38L | R-24 | R-24 | R-24 | R-24 |
|  |  | Average primary particle diameter [nm] | 230 | 260 | 290 | 400 | 200 | 200 | 200 | 200 |
|  |  | Content [parts by mass] | 24.0 | 24.0 | 24.0 | 24.0 | 24.0 | 24.0 | 24.0 | 24.0 |
|  | Component (D) | Type | RX300 | RX300 | RX300 | RX300 | R976S | 300 | RX380S | QSG-100 |
|  |  | Average primary particle diameter [nm] | 7 | 7 | 7 | 7 | 7 | 7 | 5 | 110 |
|  |  | Degree of MeOH hydrophobicity [%] | 35 | 35 | 35 | 35 | 34 | 0 | 32 | 67 |
|  |  | Content [parts by mass] | 18.0 | 18.0 | 18.0 | 18.0 | 18.0 | 18.0 | 18.0 | 18.0 |
| Evaluation |  | JIS hardness | 44 | 42 | 40 | 38 | 44 | 47 | 45 | 37 |
|  |  | Tear strength [N/cm] | 36 | 34 | 30 | 23 | 38 | 42 | 47 | 13 |
|  |  | Ethanol swelling degree [% by mass] | 8 | 8 | 8 | 10 | 8 | 10 | 8 | 7 |
|  |  | Total light reflectance [%] | 97 | 97 | 98 | 99 | 97 | 97 | 97 | 97 |
|  |  | Acoustic impedance [×$10^6$ kg/m²/sec] | 1.37 | 1.37 | 1.37 | 1.36 | 1.37 | 1.37 | 1.37 | 1.37 |
|  |  | Acoustic (ultrasonic) sensivity [dB] | −71.6 | −71.9 | −72.3 | −73.0 | −71.6 | −72.5 | −70.1 | −71.5 |

|  |  |  | Example 17 | Example 18 | Example 19 | Example 20 | Comparative Example 1 | Comparative Example 2 | Comparative Example 3 |
|---|---|---|---|---|---|---|---|---|---|
| Mixed composition | Component (A) | Type | PDV-0541 | PDV-0541 | PDV-0541 | PDV-0541 | PDV-0541 | PDV-0541 | PDV-0541 |
|  |  | Molecular weight | 60,000 | 60,000 | 60,000 | 60,000 | 60,000 | 60,000 | 60,000 |
|  |  | Content [parts by mass] | 57.4 | 57.4 | 57.4 | 57.4 | 80.9 | 75.2 | 57.4 |
|  | Component (B) | Type | HMS-991 | HMS-991 | HMS-991 | HMS-991 | HMS-991 | HMS-991 | HMS-991 |
|  |  | Molecular weight | 1,600 | 1,600 | 1,600 | 1,600 | 1,600 | 1,600 | 1,600 |
|  |  | Content [parts by mass] | 0.6 | 0.6 | 0.6 | 0.6 | 1.1 | 0.8 | 0.6 |
|  | Component (C) | Type | R-24 | Ft-24 | R-24 | R-24 | — | R-24 | AO-502 |
|  |  | Average primary particle diameter [nm] | 200 | 200 | 200 | 200 |  | 200 | 700 |
|  |  | Content [parts by mass] | 24.0 | 24.0 | 18.0 | 12.0 |  | 24.0 | 24.0 |
|  | Component (D) | Type | QSG-80 | QSG-80 | QSG-80 | QSG-80 | RX300 | — | RX300 |
|  |  | Average primary particle diameter [nm] | 80 | 30 | 30 | 30 | 7 |  | 7 |
|  |  | Degree of MeOH hydrophobicity [%] | 67 | 67 | 67 | 67 | 35 |  | 35 |
|  |  | Content [parts by mass] | 18.0 | 18.0 | 24.0 | 30.0 | 18.0 |  | 18.0 |
| Evaluation |  | JIS hardness | 40 | 42 | 43 | 45 | 41 | 34 | 42 |
|  |  | Tear strength [N/cm] | 26 | 37 | 42 | 52 | 31 | 7 | 22 |
|  |  | Ethanol swelling degree [% by mass] | 6 | 6 | 6 | 5 | 12 | 10 | 11 |

TABLE 1-continued

| Total light reflectance [%] | 97 | 97 | 97 | 96 | 31 | 95 | 92 |
|---|---|---|---|---|---|---|---|
| Acoustic impedance [×10$^6$ kg/m$^2$/sec] | 1.37 | 1.37 | 1.37 | 1.36 | 1.11 | 1.18 | 1.34 |
| Acoustic (ultrasonic) sensitivity [dB] | −70.3 | −71.0 | −70.1 | −69.2 | −68.3 | −70.1 | −73.3 |

<Notes of Table>
[Polysiloxane (Component (A))]
PDV-0541: trade name, vinyl terminated diphenylsiloxane-dimethylsiloxane copolymer manufactured by GELEST, INC., diphenylsiloxane amount of 5 mol %
PDV-0535: trade name, vinyl terminated diphenylsiloxane-dimethylsiloxane copolymer manufactured by GELEST, INC., diphenylsiloxane amount of 5 mol %
PDV-1641: trade name, vinyl terminated diphenylsiloxane-dimethylsiloxane copolymer manufactured by GELEST, INC., diphenylsiloxane amount of 16 mol %
PDV-1635: trade name, vinyl terminated diphenylsiloxane-dimethylsiloxane copolymer manufactured by GELEST, INC., diphenylsiloxane amount of 16 mol %
PDV-1631: trade name, vinyl terminated diphenylsiloxane-dimethylsiloxane copolymer manufactured by GELEST, INC., diphenylsiloxane amount of 16 mol %
[Polysiloxane (Component (B))]
HMS-991: trade name, methylhydrosiloxane polymer manufactured by GELEST, INC., Si—H equivalent of 67 g/mol
HPM-502: trade name, methylhydrosiloxane-phenylmethylsiloxane copolymer manufactured by GELEST, INC., Si—H equivalent of 165 g/mol
[Titanium Oxide Particle (Component (C))]
R-24: "TITONE R-24" (trade name) manufactured by Sakai Chemical Industry Co., silica-alumina-organic surface treatment
R-3 L SN: "R-3 L SN" (trade name) manufactured by Sakai Chemical Industry Co., silica-alumina-organic surface treatment
D-962: "D-962" (trade name) manufactured by Sakai Chemical Industry Co., silica-alumina-organic surface treatment
R-45M: "TITONE R-45M" (trade name) manufactured by Sakai Chemical Industry Co., silica-alumina surface treatment
R-38L: "TITONE R-38L" (trade name) manufactured by Sakai Chemical Industry Co., zirconia-alumina surface treatment
[Silica (Component (D))]
True spherical shape: having Wardell's sphericity of 0.9 to 1
Heteromorphic shape: having Wardell's sphericity of less than 0.9
RX300: "AEROSIL (registered trademark) RX300" (trade name) manufactured by NIPPON AEROSIL CO., LTD., hexamethyldisilazane (HMDS)-surface-treated product, irregular form
R 976 S: "AEROSIL (registered trademark) R 976 S" (trade name) manufactured by NIPPON AEROSIL CO., LTD., dimethyldichlorosilane (DDS)-surface-treated product, irregular form
300: "AEROSIL (registered trademark) 300" (trade name) manufactured by NIPPON AEROSIL CO., LTD., no surface treatment, irregular form
RX 380S: "AEROSIL (registered trademark) RX 380S" manufactured by NIPPON AEROSIL CO., LTD., HMDS-surface-treated product, irregular form
QSG-100: trade name, manufactured by Shin-Etsu Chemical Co., Ltd., methyltrimethoxysilane (MTMS) and HMDS-surface-treated product, truly spherical shape
QSG-80: trade name, manufactured by Shin-Etsu Chemical Co., Ltd., MTMS and HMDS-surface-treated product, truly spherical shape
QSG-30: trade name, manufactured by Shin-Etsu Chemical Co., Ltd., MTMS and HMDS-surface-treated product, truly spherical shape
[Other Components]
AO-502: "ADMAFINE (registered trademark) AO-502" manufactured by Admatechs, alumina oxide As is clear from Table 1, in all of the silicone resin sheets of Examples 1 to 20 formed of the composition for an acoustic wave probe of the embodiment of the present invention which contains the titanium oxide particles and the silica particles, the acoustic impedance value was close to that of the living body, the acoustic attenuation was suppressed to be low, the resin hardness and tear strength were high, the total light reflectance was high, the degree of ethanol swelling was low, and the chemical resistance was excellent.

On the other hand, in the silicone resin sheet formed of the composition for an acoustic wave probe of Comparative Example 1 which does not contain the titanium oxide particles, the acoustic impedance value was smaller than that of the living body, the total light reflectance was also low, the degree of ethanol swelling was high, and the chemical resistance was not excellent.

In addition, in the silicone resin sheet formed of the composition for an acoustic wave probe of Comparative Example 2 which does not contain the silica particles, the acoustic impedance value was smaller than that of the living body.

Furthermore, in the silicone resin sheet formed of the composition for an acoustic wave probe of Comparative Example 3 which contains the titanium oxide particles, and the oxidized alumina particles as a substitute for the titanium oxide particles, the total light reflectance was low, the degree of ethanol swelling was high, and the chemical resistance was not excellent.

From the results, it can be seen that the composition for an acoustic wave probe of the embodiment of the present invention is useful for a medical member. In addition, it can be seen that the silicone resin for an acoustic wave probe of the embodiment of the present invention can also be suitably used in the acoustic lens and/or the acoustic matching layer of the acoustic wave probe, the acoustic wave measurement apparatus, and the ultrasound diagnostic apparatus. Particularly, the composition for an acoustic wave probe and the silicone resin for an acoustic wave probe can be suitably used in the ultrasound probe in which cMUT is used as an ultrasonic transducer array, the photoacoustic wave measurement apparatus, and the ultrasound endoscope for the purpose of improving the sensitivity.

The present invention has been described using an embodiment thereof. However, it is considered that, unless otherwise specified, even the detailed description of the invention is not limited and is necessarily widely interpreted without departing from the gist and the range of the invention shown in the attached claims.

Explanation of References 1: acoustic lens
2: acoustic matching layer
3: piezoelectric element layer
4: backing material
7: housing
9: cord
10: ultrasound probe (probe)

What is claimed is:

1. A composition for an acoustic wave probe, comprising:
   polysiloxane (A) that has a vinyl group and a phenyl group;
   polysiloxane (B) that has two or more Si—H groups in a molecular chain;
   a titanium oxide particle (C); and
   a silica particle (D),
   wherein at least one of the titanium oxide particle (C) or the silica particle (D) is a particle subjected to surface treatment,
   wherein the component (D) is a particle subjected to surface treatment using a silicon compound, and
   wherein the component (D) subjected to surface treatment is truly spherical.

2. The composition for an acoustic wave probe according to claim 1,
   wherein 0.1 to 60 parts by mass in total of the component (C) and the component (D) are contained in 100 parts by mass in total of the components (A) to (D).

3. The composition for an acoustic wave probe according to claim 1, wherein 10 to 99.4 parts by mass of the component (A) and 0.5 to 90 parts by mass of the component (B) are contained in 100 parts by mass in total of the components (A) to (D).

4. The composition for an acoustic wave probe according to claim 1, wherein an average primary particle diameter of the component (C) is 100 to 300 nm.

5. The composition for an acoustic wave probe according to claim 1, wherein the component (C) is a particle subjected to surface treatment using a silicon compound.

6. The composition for an acoustic wave probe according to claim 1,
   wherein the component (D) is a particle subjected to surface treatment using a silane compound.

7. The composition for an acoustic wave probe according to claim 6,
   wherein the component (D) is a particle subjected to surface treatment using a trimethylsilylating agent.

8. The composition for an acoustic wave probe according to claim 1,
   wherein a degree of methanol hydrophobicity of the component (D) subjected to surface treatment is 40% to 80% by mass.

9. The composition for an acoustic wave probe according to claim 1,
   wherein a mass average molecular weight of the component (A) is from 20,000 to 200,000.

10. The composition for an acoustic wave probe according to claim 9,
    wherein the mass average molecular weight of the component (A) is from 40,000 to 150,000.

11. The composition for an acoustic wave probe according to claim 1,
    wherein the component (B) is a compound containing a phenyl group.

12. The composition for an acoustic wave probe according to claim 1, further comprising:
    0.00001 to 0.01 parts by mass of platinum or a platinum compound with respect to 100 parts by mass in total of the components (A) to (D).

13. A silicone resin for an acoustic wave probe which is obtained by vulcanizing the composition for an acoustic wave probe according to claim 1.

14. An acoustic wave probe comprising:
    an acoustic lens and/or an acoustic matching layer made of the silicone resin for an acoustic wave probe according to claim 13.

15. An ultrasound probe comprising:
    a capacitive micromachined ultrasonic transducer as an ultrasonic transducer array; and
    an acoustic lens made of the silicone resin for an acoustic wave probe according to claim 13.

16. An acoustic wave measurement apparatus comprising:
    the acoustic wave probe according to claim 14.

17. An ultrasound diagnostic apparatus comprising:
    the acoustic wave probe according to claim 14.

18. A photoacoustic wave measurement apparatus comprising:
    an acoustic lens made of the silicone resin for an acoustic wave probe according to claim 13.

19. An ultrasound endoscope comprising:
    an acoustic lens made of the silicone resin for an acoustic wave probe according to claim 13.

* * * * *